United States Patent [19]

Braatz

[11] 4,302,980
[45] Dec. 1, 1981

[54] ANESTHESIA MACHINE WITH MODULAR FLOWMETERS

[75] Inventor: Robert E. Braatz, Sun Prairie, Wis.
[73] Assignee: Airco, Inc., Montvale, N.J.
[21] Appl. No.: 86,963
[22] Filed: Oct. 19, 1979
[51] Int. Cl.³ .............................................. G01F 1/22
[52] U.S. Cl. ................................................. 73/861.55
[58] Field of Search ............... 73/861.55, 861.56, 195, 73/201, 273; 128/204.18, 205.23

[56] References Cited

U.S. PATENT DOCUMENTS

| | | | |
|---|---|---|---|
| 2,310,021 | 2/1943 | Heidbrink | 128/204.18 |
| 3,021,840 | 2/1962 | Hallamore et al. | 128/200.21 |
| 3,232,106 | 2/1966 | Busillo | 73/861.55 |
| 3,691,835 | 9/1972 | Metzger | 73/861.55 |

OTHER PUBLICATIONS

Foregger Co., Catalog 17, 1962, pp. 2-4.

*Primary Examiner*—Herbert Goldstein
*Attorney, Agent, or Firm*—Roger M. Rathbun; Larry R. Cassett

[57] ABSTRACT

An anesthesia machine is disclosed wherein flowmeters used to denote flow of O₂ and other gases are in the form of precalibrated modules. The modules each contain a flowtube, float and scale and are precalibrated and the modules sealed to prevent tampering or affecting the calibration. The flowmeter modules are thus readily inserted into or removed from the anesthesia machine by a single plug-in maneuver to a common manifold without further calibration or leak testing. A key index system prevents the mislocation of any particular flowmeter module in a machine.

The flowmeter module has a lower manifold at its bottom where all plug-in connections are located. A flowtube containing the float extends upwardly from the manifold and has an easily visible scale for accurate readings. Internal tubing within the flowmeter module returns gas from the flowtube back to the outlet connection in the lower manifold. The flowmeter modules may be, therefore, completely tested for leaks, calibrated at the source and tamperproof measures included to prevent disassembly or in any way upsetting the calibration short of factory rebuilding the flowmeter module. Because the units are factory sealed, replacement of flowmeter modules may be made by personnel in the field unskilled with such machines.

2 Claims, 5 Drawing Figures

FIG. 2
FIG. 3
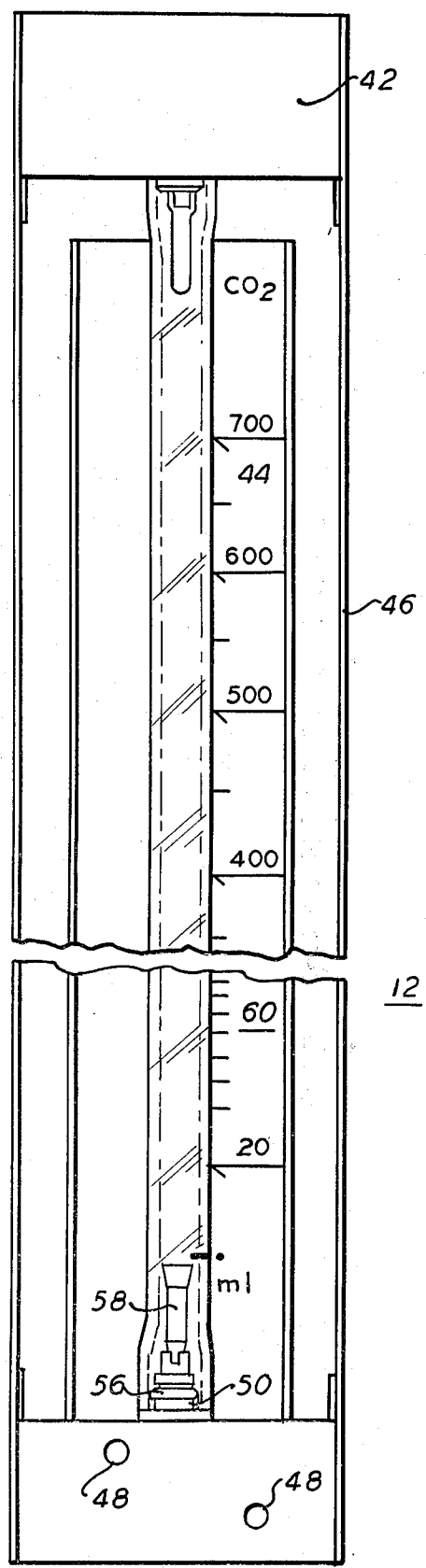
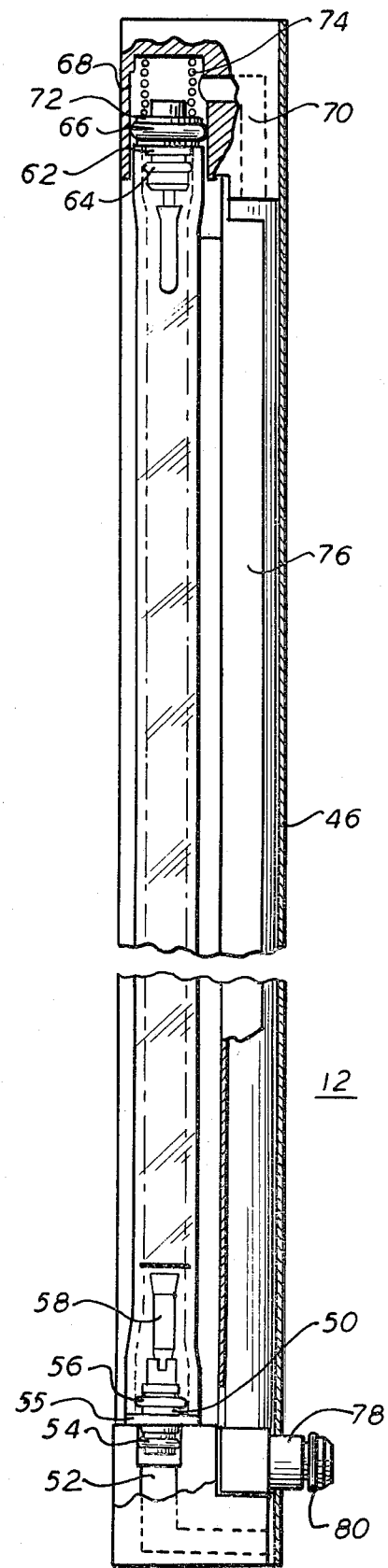

ANESTHESIA MACHINE WITH MODULAR FLOWMETERS

BACKGROUND OF THE INVENTION

This invention relates to an anesthesia machine, and more particularly, to an improved anesthesia machine wherein flowmeters are provided in the form of calibrated flowmeter modules including flowtubes floats and scales and wherein the flowmeter module is sealed with preventative means to discourage any alteration which could affect such calibration and integrity of the flowmeter module.

At present, normal anesthesia machines contain a plurality of needle valves for controlling the flow of oxygen and other various gases that are used to make up a respirable mixture for administration to a patient.

In addition to needle valves for such control, it is common to feature flowmeters including flowtubes, floats and flow scales through which the individual gases pass and which give the user a visual indication of the actual flow of that gas through the machine. It is not uncommon for such anesthesia machine to provide needle valves and flowmeters for gases including oxygen, nitrous oxide, $CO_2$, helium and the like with individual control for each.

Such flowmeters include flowtubes that normally receive the gas at their bottom of such flowtubes and discharge the same at their top, and wherein a floating indicator within the flowtubes can be read from a scale located adjacent the tube. The tubes are individually calibrated and their installation and removal custom done, that is, the removal and replacement of any particular flowmeter requires skilled personnel accustomed to handling such equipment and further requires a recalibration of the flowmeter itself.

Because such flowmeters are individually factory installed and calibrated, there is considerable expense in manufacturing such anesthesia machines and, of course, in the later replacement and recalibration of any particular flowmeter.

SUMMARY OF THE INVENTION

There is herein described an anesthesia machine wherein the flowmeters are provided in the form of plug-in modules and wherein such flowmeters are basically self-contained and are leak tested, calibrated and sealed at the factory. The flowmeter modules are readily installed and removed from the anesthesia machine by fairly unskilled personnel.

The flowmeter modules are individually keyed to a common manifold such that once the keying arrangement has been determined, only that flowmeter module, calibrated for a particular gas, can thereafter be replaced by one for that same gas. Thus, a flowmeter module calibrated for $CO_2$ cannot inadvertently be placed into an anesthesia machine in a position intended for oxygen.

The flowmeter modules allow ease of manufacture since common parts may be utilized in many instances and all can be calibrated and leak tested right at the factory and are provided with protective features to discourage tampering such that the flowmeter modules can thereafter be installed in the field without further calibration or testing.

The flowmeter modules themselves have a lower manifold which contains the plug-in fittings for the flowmeter inlet and outlet since all other necessary flow tubing is self-contained with the flowmeter modules. This facilitates the use of a single gas manifold on the anesthesia machine into which the individual flowmeter modules are adapted to be plugged and therefore avoids the necessity of both a lower manifold and an upper manifold on the anesthesia machine.

Once the flowmeter modules have been factory calibrated, the flowtubes, scales and floats are inseparable by certain deterrents to insure the integrity of their calibration.

The removal of a flowmeter module also makes it readily available for rebuilding the same while minimizing down time of the anesthesia machine due to the ease of installing another flowmeter module to continue the use of that anesthesia machine. Thus, the anesthesia machine can have its individual flowmeters repaired, either separately or all at once, without removing that anesthesia machine from service. A hospital may therefore inventory additional flowmeter modules rather than require the presence of backup anesthesia machines.

BRIEF DESCRIPTION OF THE DRAWINGS

The invention is diagrammatically illustrated by way of example, in the drawings appended hereto, in which:

FIG. 2 is a front view of one of the flowmeter modules used in the anesthesia machine of FIG. 1;

FIG. 3 is a side view, partly in cross-section of the flowmeter module of FIG. 2;

DESCRIPTION OF THE PREFERRED EMBODIMENT

Figure 1:
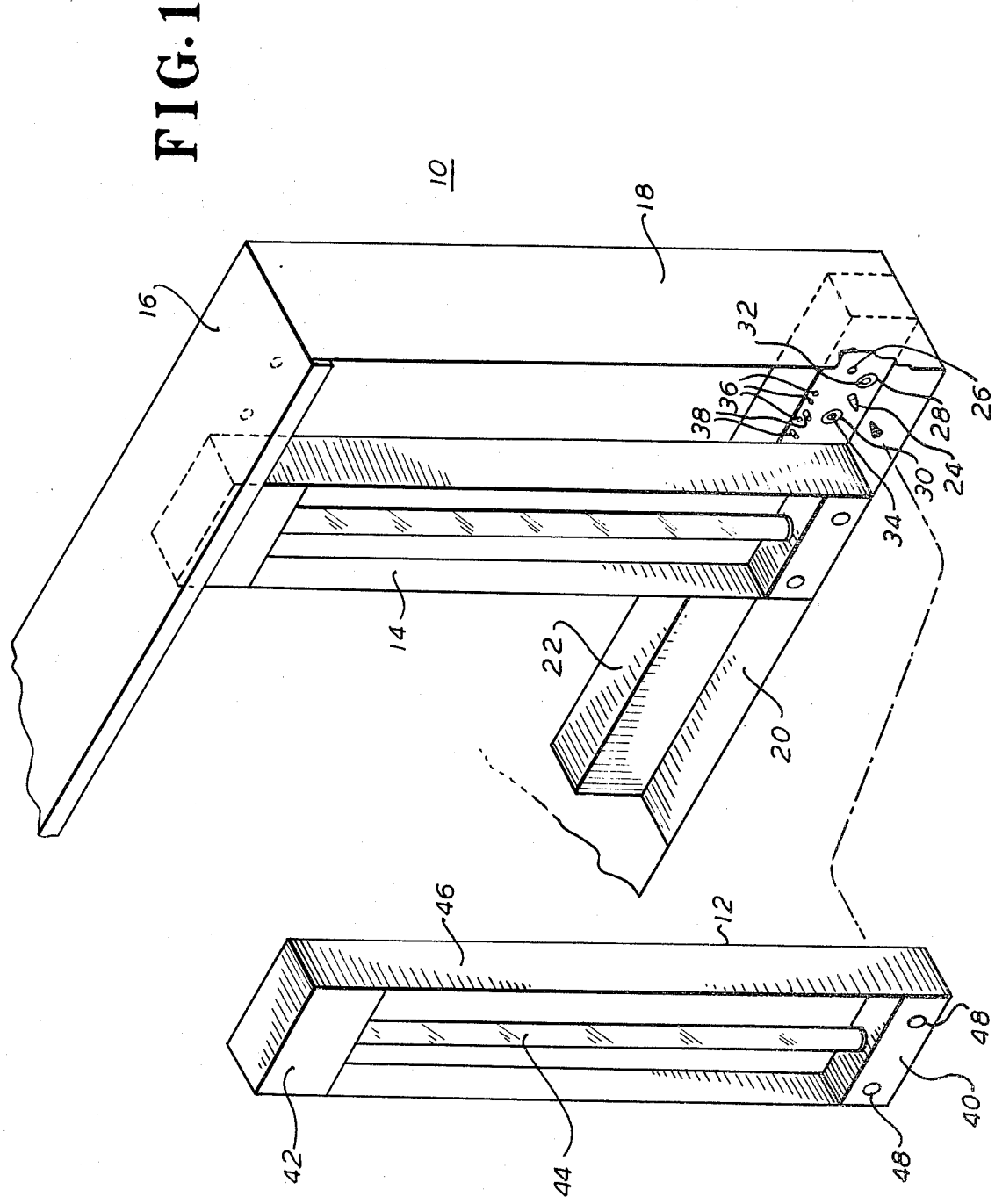
FIG. 1 is an isometric view showing an anesthesia machine of the present invention having a flowmeter module installed thereon; and having a flowmeter module shown removed therefrom.

Turning first to FIG. 1, there is shown an isometric view of a portion of an anesthesia machine 10 having a flowmeter module 12, shown separated therefrom, and a flowmeter module 14 mounted in place on the anesthesia machine 10.

Basically, the anesthesia machine 10 is not shown in detail and normally contains considerable additional structure and equipment, including needle valves, flow tubing and the like. As shown, however, the anesthesia machine 10 has a top frame member 16, side frame member 18 and bottom frame member 20.

A specially constructed manifold 22 is positioned at the lower end of anesthesia machine 10 and is adapted to receive a flowmeter module, such as 12, by a simple plug-in connection.

As shown in the position on the anesthesia machine 10 wherein the flowmeter module 12 is shown removed, there is a nipple 24 having an O-ring encircled thereabout for sealing the nipple 24 when it is inserted into a corresponding hole in flowmeter module 12 when the flowmeter module 12 is placed into operating position. A hole 26 is also formed in the manifold 22 and, as will be later shown, receives a suitable nipple on the flowmeter module 12.

A pair of circular recesses 28 and 30 are also formed in manifold 22 and will be later explained, however, the circular recesses 28 and 30 have smaller threaded holes 32 and 34 in manifold 22.

A keying system is utilized to assure that the proper flowmeter module is inserted in the correct position on an anesthesia machine. The keying system is shown in FIG. 1 as a plurality of holes 36 drilled into manifold 22 in a predetermined position. These holes 36 are adapted to receive one or more pins 38 and which are forced into the holes 36 in a predetermined position, depending upon the sequence for the particular gas to be used at that position.

In FIG. 1, there are two such pins 38 shown protruding from two of the holes 36. When inserted during the manufacture of such anesthesia machines, the pins 38 are permanently forced into holes 36 such that they cannot be thereafter removed without considerable difficulty.

The flowmeter module 12 includes a lower manifold 40, an upper manifold 42 and a flowtube 44 therebetween. A C-shaped shroud 46 partially encloses the upper and lower manifolds 42 and 40. A pair of holes 48 are drilled through the lower manifold 40 and which receive screws (not shown) that hold the flowmeter module 12 to the manifold 22 of the anesthesia machine 10.

Turning now to FIGS. 2 and 3, there is shown a front and side view, partly in cross-section, of a flowmeter module 12. At the bottom of the flowtube 44, an inlet 50 is positioned as shown, and which receives the gas to be measured from passageway 52 in lower manifold 40. The inlet 50 is sealed against the passageway 52 by means of O-ring 54 and likewise, is sealed within the interior of flowtube 44 by means of another O-ring 56. Inlet 50 additionally includes a larger diameter flange 55 which provides a seat for the flowtube 44 so that the flowtube 44 does not rest directly on the lower manifold 40, the lower manifold 40 being preferably of a metal. The inlet 50, however, can readily be formed of plastic. Nestled within inlet 50 is the floating indicator 58 and which actually rests upon the inlet 50 during no flow conditions. The floating indicator 58 is basically of conventional design and rises within flowtube 44 as the flow of gas through flowtube 44 is increased. The position of floating indicator 58 is, therefore, indicative of such flow and can be read from scale 60. As one of the features of this invention, scale 60 is positioned with respect to the flowtube 44 in order to calibrate the flowmeter module 44. Thus, the flowmeter module 12 provides factory calibration and is installable, without further calibration or leak testing, by relatively unskilled personnel in an anesthesia machine in a hospital without requiring the removal of that anesthesia machine from service for any appreciable length of time.

At the top of flowtube 44 there is an outlet 62 which conducts the gas leaving flowtube 44 into the upper manifold 42. The outlet 62 is also preferably a plastic element and has an O-ring 64 which seals the outlet 62 within the interior of flowtube 44. A further O-ring 66 seals the outlet 62 against the interior bored hole 68 in upper manifold 42 and which receives the gas from flowtube 44 whereupon it enters passageway 70.

The outlet 62 also has an enlarged circular flange 72 that bears against the upper open end of flowtube 44. A spring 74 exerts a bias against the outlet 62 having one end thereof fixed at the upper closed end of interior bored hole 68 and the other end thereof bearing on and exerting the bias against enlarged circular flange 72 of the outlet 62. In this manner, the flowtube 44 is continually biased through its bottom forced against the large diameter flange 55 such that the flowtube 44 is easily retained in position without undue compression against its ends that could cause breakage.

The passageway 70 connects to a flexible tube 76, which conducts the gas back to the lower manifold 40 where the flexible tube 76 connects to outlet nipple 78. Outlet nipple 78 includes an O-ring 80 that provides a seal for outlet nipple 78 when the flowmeter module 12 is operatively installed in anesthesia machine 10.

Figure 4:
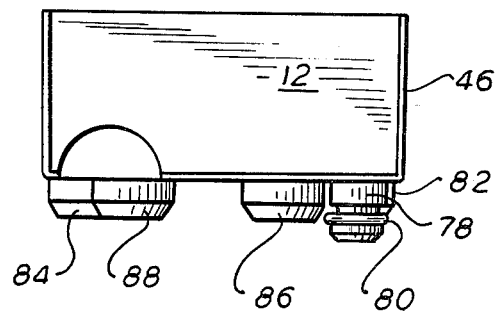
FIG. 4 is a rear view of the flowmeter module of FIG. 2.

In FIG. 4, there is shown a bottom view of the flowmeter module 12 and having outlet nipple 78 showing the profiles of projecting stubs 82, 84, 86 and 88.

Figure 5:
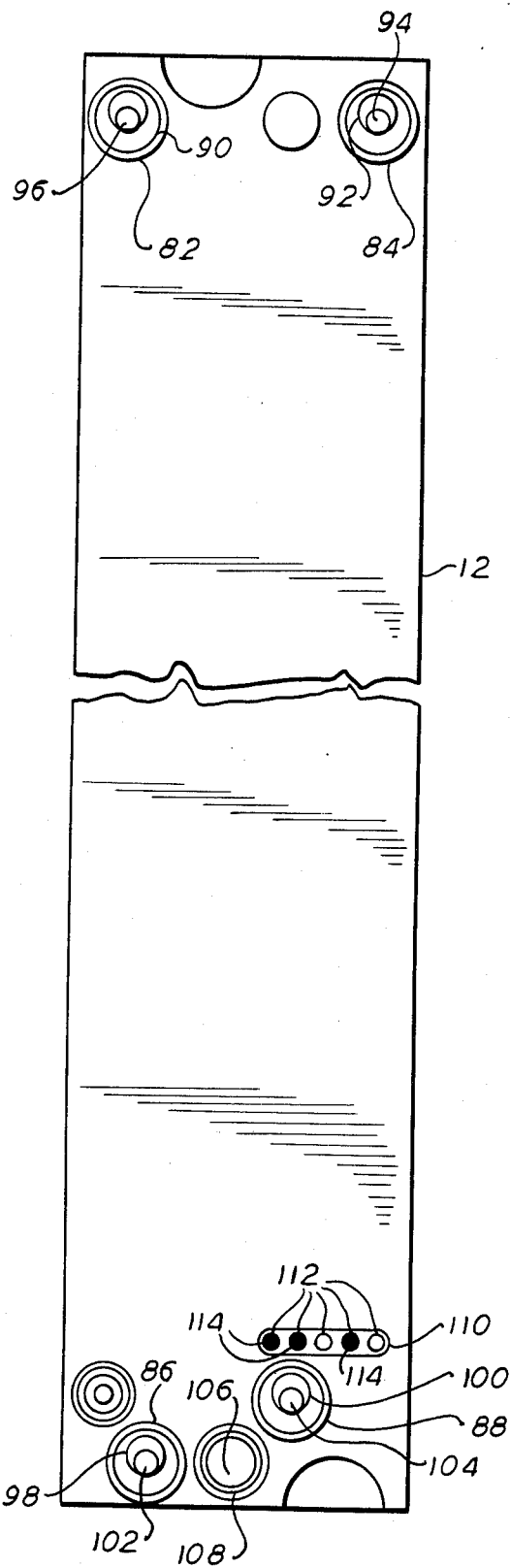
FIG. 5 is a bottom view of the flowmeter module of FIG. 2.

Turning to FIG. 5, a rear view of the flowmeter module 12 is shown having the C-shaped shroud 46 in place. The projecting stubs 82 and 84 are located at the top of the flowmeter module 12. Each of the projecting stubs 82 and 84 have off-center holes 90, 92 which are adapted to receive a special wrench which prevents unauthorized removal of the projecting stubs 82 and 84. The projecting stubs 82 and 84 have threaded ends that are screwed into upper manifold 42 to retain the same within C-shaped shroud 46. The projecting stubs 82 and 84 also have central holes 94 and 96.

At the bottom of the flowmeter module 12, the projecting stubs 86 and 88 also have off-center holes 98, 100 which serve the same purpose as the similar off-center holes 90 and 92 previously discussed. The projecting stubs 86 and 88 further have central holes 102, 104 and which receive screws for installing flowmeter module 12 to anesthesia machine 10 in a manner to be later explained.

The flowmeter module inlet 106 is provided in the rear of flowmeter module 12 and is an opening which seals against an O-ring on nipple 24 (FIG. 1) when the flowmeter module 12 is assembled to anesthesia machine 10.

An oval shaped opening 110 in the C-shaped shroud allows access to the keying system. As noted, the keying system includes a plurality of drilled holes 112 in the lower manifold 40 of the flowmeter module 12. As shown, five drilled holes 112 are used, but it may easily be seen that more or less holes may be utilized and still produce a viable keying system.

In one or more of the drilled holes 112, a plug 114 is forced thereinto and, when so inserted, is roughly flush with the outside opening of drilled holes 112. As shown, and again merely by way of illustration, three plugs 114 are utilized, however, again, the numbering and location of plugs 114 are a matter of selection. It is suffice to say that in any such systems, the number and location of plugs 114 is such that the same sequence be chosen for only one gas and that sequence carried out on all further flowmeter modules manufactured and calibrated for that particular gas.

In the assembly of flowmeter module 12 to the anesthesia machine 10, turning back to FIG. 1 taken in conjunction with FIG. 5, the flowmeter module 12 is plugged into the manifold 22, providing the keying system is compatible, i.e. the flowmeter module for a particular gas is properly assembled to the corresponding position on the anesthesia machine 10 for that gas.

In the embodiment illustrated, the pins 38 fit within the two drilled holes 112 where there are no plugs 114. Since the two systems are, therefore, compatible, the flowmeter module 12 may have its outlet nipple 78 fitted within hole 26 in the manifold 22 and, similarly, the nipple 24 on the manifold 22 fits within the flowmeter module inlet 106 so that gas piped to the manifold 22 can enter the flowmeter module 12 and be received therefrom after passing through the flowtube 44 where floating indicator 58 may be viewed to read the flow of gas from scale 60.

As also may be seen, in installing flowmeter module 12, the projecting stubs 86 and 88 fit within circular recesses 28 and 30 and further serve to align the flowmeter module 12 on to the anesthesia machine 10. Screws, not shown, then pass through the central holes 48 and engage the threads within threaded holes 32 and 34 in circular recesses 28 and 30. It should be noted that a further safety feature is included to prevent incapacitating or defeating the keying system, in that the screws are of a predetermined length such that they will not begin to engage any threads within threaded holes 32 and 34 unless the proper pins on manifold 22 are aligned with open holes in flowmeter module 12 in the keying system and are inserted therein. This prevents personnel from using the screws to create a sufficient force to distort the pins and defeat the purpose of the keying system.

A further screw (not shown) is utilized at the top of the flowmeter module 22 and screws from the back of the anesthesia machine 10 through a suitable frame member into the central hole 96 of projecting stub 82 and into a threaded hole in the upper manifold 42, thereby securing the top of the flowmeter module 22 in position.

It will be understood that the scope of the method and product of this invention is not limited to the particular steps or materials disclosed herein, by way of example, but only by the scope of the appended claims.

I claim:

1. A precalibrated flowmeter module for assembly in an anesthesia machine, said flowmeter module comprising a lower manifold, inlet means and outlet means in said lower manifold adapted to receive and discharge, respectively, a gas, a flowtube, a floating indicator within said flowtube and a scale to record the position of said floating indicator, said flowtube, floating indicator and scale being calibrated by the position of said scale, said lower manifold further comprising a flowtube inlet for introducing the gas into said flowtube, an upper manifold, and a flowtube outlet in said upper manifold for receiving gas from said flowtube, tubing means connecting said flowtube outlet with said outlet means, said flowmeter module further having a C-shaped shroud, protective means affixing said shroud to said upper and lower manifolds enclosing said module to inhibit removal of said shroud and disassembly of said flowtube, floating indicator and said scale.

2. A precalibrated flowmeter module as defined in claim 1 wherein said protective means comprises a plurality of projecting stubs threadedly engaged to said upper and lower manifolds, said stubs having external off-center holes adapted to receive a special wrench for rotating said stubs.

* * * * *